(12) United States Patent
Huhtelin et al.

(10) Patent No.: US 6,328,851 B1
(45) Date of Patent: Dec. 11, 2001

(54) METHOD AND EQUIPMENT FOR CONTROLLING PROPERTIES OF PAPER

(75) Inventors: Taisto Huhtelin; Risto Kuusisto; Lin Tian; Timo Rantala, all of Tampere; Jukka Nokelainen, Kajaani, all of (FI)

(73) Assignee: Metso Paper Automation OY, Tampere (FI)

( * ) Notice: Subject to any disclaimer, the term of this patent is extended or adjusted under 35 U.S.C. 154(b) by 0 days.

(21) Appl. No.: 09/193,428

(22) Filed: Nov. 17, 1998

(30) Foreign Application Priority Data

Nov. 25, 1997 (FI) ........................................ 974328

(51) Int. Cl.⁷ ................... D21F 1/06; D21F 1/08
(52) U.S. Cl. .................... 162/198; 162/190; 162/258; 162/259; 162/263; 162/DIG. 6; 162/DIG. 11; 700/128
(58) Field of Search .................... 162/198, 189, 162/190, 258, 259, 263, 264, DIG. 6, DIG. 10, DIG. 11; 700/127–129

(56) References Cited

FOREIGN PATENT DOCUMENTS 495400   12/1975   (SU) .

OTHER PUBLICATIONS

Camacho, E.F., et al., Model Predictive Control in The Process Industry (1995, Springer Verlag London Limited.

David Clarke, "Advances in Model–Based Predictive Control" Oxford University Press 1994.

I.C. Roberts, "Paper Chemistry" Blackie Academic and Professional 1996.

Haggman, Borje "Matematiska modeller for pappersmaskiner." Svensk Papperstidning, vol. 79 (1976) pp 44–49.

Dorozhinskii, Y. B., "Method of Automatically Controlling Stock Flow to the Paper Machine Wire." Otkryt. Izobret, 52 No. 46: 74 (1975) RU–C–495400.

Nokelainen, Jukka "Lyhyen Kierron Sakeussaadot." AEL/INSKO P906202/96 V (1996).

*Primary Examiner*—Jose Fortuna
(74) *Attorney, Agent, or Firm*—Ladas & Parry

(57) ABSTRACT

The invention relates to a method and equipment for controlling properties of paper, in which method the effect of the flow of retention agent ($F_{ra}$) and the stock flow ($F_{ts}$) on the basis weight of the paper (BW) is modelled. The fulfilled modelling is used to adjust the basis weight of the paper (BW) by controlling simultaneously the flow of retention agent ($F_{ra}$) and the stock flow ($F_{ts}$).

15 Claims, 1 Drawing Sheet

METHOD AND EQUIPMENT FOR CONTROLLING PROPERTIES OF PAPER

FIELD OF THE INVENTION

The invention relates to a method for controlling properties of paper, in which method the basis weight of the paper is measured and the basis weight is adjusted by controlling the stock flow on the basis of the measurement result of the paper basis weight.

The invention also relates to equipment for controlling properties of paper, comprising means for measuring the basis weight of the paper and control means for controlling the stock flow in order to adjust the basis weight based on the measurement result.

BACKGROUND

As regards controls in so-called short circulation of a paper machine, paper properties are controlled at present for example by adjusting the white water total consistency through adjustment of the flow rate of the retention agent. In such a case, the result of the measurement of the white water consistency forms the basis for controlling a retention agent pump or valve in order to adjust the flow rate of the retention agent to be supplied. Further, in the prior art the ash content of paper is controlled by measuring the ash content for example from the finished paper with a measuring beam and/or by measuring the ash content in the headbox and/or the ash content of the stock and by controlling the flow rate of the filler to be added to the stock. The basis weight of the paper is controlled by means of stock flow control, which also takes into account changes in the stock consistency on the basis of total headbox consistency and/or a measurement result obtained from the measuring beam on the basis weight of the paper. Each control operates independently regardless of the other controls. Such an arrangement is disclosed for example in the reference "Lyhyen kierron sakeussäädöt, AEL/INSKO P906202/96 V, Nokelainen J., 1996" (consistency controls in the short circulation). Controlling one property also affects other properties; for example variation in the amount of retention agent and/or filler affects the basis weight, and therefore one or more controls are adjusted to operate so slowly that they do not interfere with the faster controls. Such a slow control cannot naturally compensate for rapid changes occurring in the property it controls. On the other hand, for example during grade changes the controls are carried out at consecutive stages and therefore the total time required for the changes is rather long. The situation is especially difficult with paper grades having a considerable ash content or with paper grades utilizing coated broke, which means that the papermaking process will be subjected to problems with the ash due to variation in the amount of broke or in the ash content of the broke, since in such a case changes in the amount of retention agent strongly affect the paper ash content and, correspondingly, changes in the amount of filler strongly affect the white water consistency.

SUMMARY OF THE INVENTION

The purpose of the present invention is to provide a method and equipment for rapid and effective control of paper properties.

The method according to the invention is characterized by modelling the effect of the flow of retention agent and the stock flow on the basis weight of the paper and adjusting, on the basis of said modelling, the basis weight by simultaneously controlling the flow of retention agent and the stock flow.

Further, the equipment according to the invention is characterized in that the equipment comprises a model of the effect of the flow of retention agent and the stock flow on the basis weight of the paper, and that the control means comprise means for controlling simultaneously the flow of retention agent and the stock flow in order to adjust the basis weight of the paper based on said model.

The invention is based on the idea of modelling the effect of the amount of retention agent on the basis weight of the paper and similarly the effect of the stock flow on the basis weight of the paper, and the executed modelling is used to adjust the basis weight of the paper by controlling simultaneously the flow of retention agent and the stock flow. The idea of a preferred embodiment is to model the effect of the flows of retention agent and filler both on the amount of filler in the white water and on the paper ash content and to adjust the latter two by controlling simultaneously the flow of retention agent and the flow of filler on the basis of the modelling.

In connection with the present application, the term "paper" also refers to board in addition to paper.

The invention has the advantage that it provides faster and more effective control of paper properties in paper machine short circulation than the previous methods.

BRIEF DESCRIPTION OF THE DRAWINGS

The invention is described in more detail with reference to the accompanying drawings, in which.

DETAILED DESCRIPTION

Figure 1:
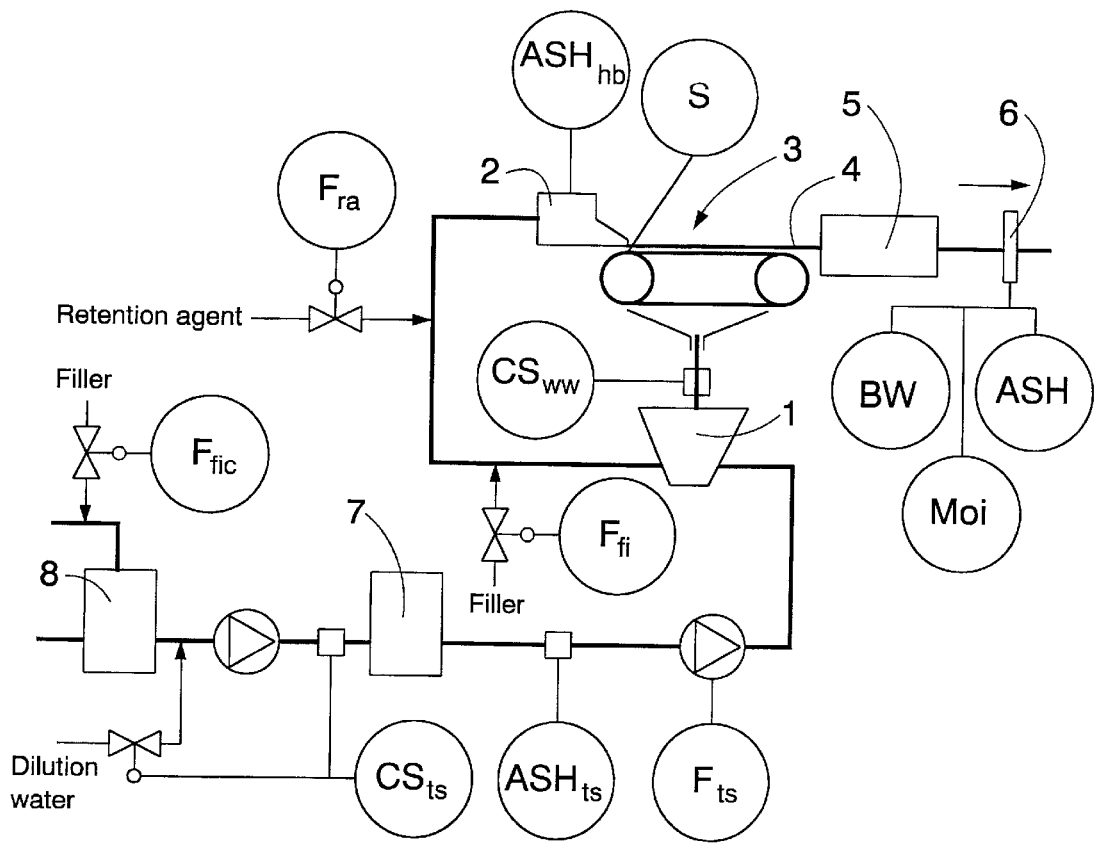
FIG. 1 shows schematically a papermaking process.

FIG. 1 shows schematically a papermaking process. Stock is supplied to a paper machine via a wire pit silo 1. Water is mixed into the stock arriving from the wire pit silo 1 in order to adjust the consistency to a suitable level. The stock is thereafter supplied to a headbox 2, from which the stock is supplied to a former section 3, where it is formed into a fibre web 4. The fibre web 4 is dried in a dryer section 5, which is followed by a measuring beam 6. The paper machine also comprises for example a press section and a reel, and it may also comprise e.g. size presses or a calender, which are not shown in the accompanying figure for the sake of clarity. Furthermore, the operation of a paper machine is known per se to a person skilled in the art and therefore it will not be described in greater detail in this connection.

For the control of paper properties according to the invention, the basis weight BW and the ash content ASH of the paper are measured from the measuring beam 6. The variable "paper ash content ASH" may be for example the proportion of ash from the basis weight or dry weight of the paper or the amount of ash, i.e. the mass flow, in a time unit. Paper moisture Moi can also be measured from the measuring beam 6 if the total ash content is to be determined, for example. Further, headbox ash content $ASH_{hb}$ and white water total consistency $CS_{ww}$ are measured. Instead of the white water total consistency $CS_{ww}$ it is possible to measure some other variable that describes the filler content of white water, such as the consistency of the bottom, top, inner or outer white water or for example the white water ash content. However, measurement of the white water total consistency $CS_{ww}$ is easy and simple. Disturbance variables that are measured for the purpose of optimization include the machine speed S and the stock ash content $ASH_{ts}$. The machine speed S can be measured from either one or several points, for example from the former section 3 or the reel or from both points. Instead of the stock ash content $ASH_{ts}$ it is possible to use a value calculated for the mass flow of the stock ash content $QA_{ts}$ such that $$QA_{ts}=F_{ts}*CS_{ts}*ASH_{ts},$$

wherein $QA_{ts}$ is the mass flow of the stock ash content,
$F_{ts}$ is the stock flow,
$CS_{ts}$ is the total consistency of stock, and
$ASH_{ts}$ is the stock ash content.

The total consistency of stock $CS_{ts}$ is usually standardized with a separate control provided before a machine chest 7, but in the optimum control according to the invention the total consistency of stock $CS_{ts}$ is also introduced into the process as a disturbance variable.

According to the invention, the flow of retention agent $F_{ra}$ is controlled by a flow regulator. Retention agents increase the retention of fines and fillers and simultaneously speed up drainage in a manner known per se. Retention agents may be inorganic retention agents, natural organic retention agents or synthetic water-soluble organic polymers in a manner known per se. Further, the stock flow $F_{ts}$ is controlled by a separate flow regulator.

If desired, the control system according to the invention can be used to simultaneously adjust the flow of filler $F_{fi}$ with a flow regulator. The purpose of a filler is, among other things, to improve paper formation, surface properties, opacity, brightness and printability and to decrease manufacturing costs. A filler may be, for example, kaolin, calcium carbonate, titanium dioxide or talc in a manner known per se. A flow regulator that is used to control the flow of retention agent or filler or the stock flow can be for example a valve or a use-controlled pump or both. Flow adjustment and control refer in the present application specifically to controlling the flow rate, which can be denoted for example in the following manners that are known per se: l/min or g/ton of production.

If there is no control of the flow of filler $F_{fi}$ the flow of constant filler $F_{fic}$ to be supplied to a mixing tank 8 can be controlled instead. However, in such a case it is necessary to take into account an additional time constant and therefore the accuracy of the final control may not necessarily be very good.

Figure 2:
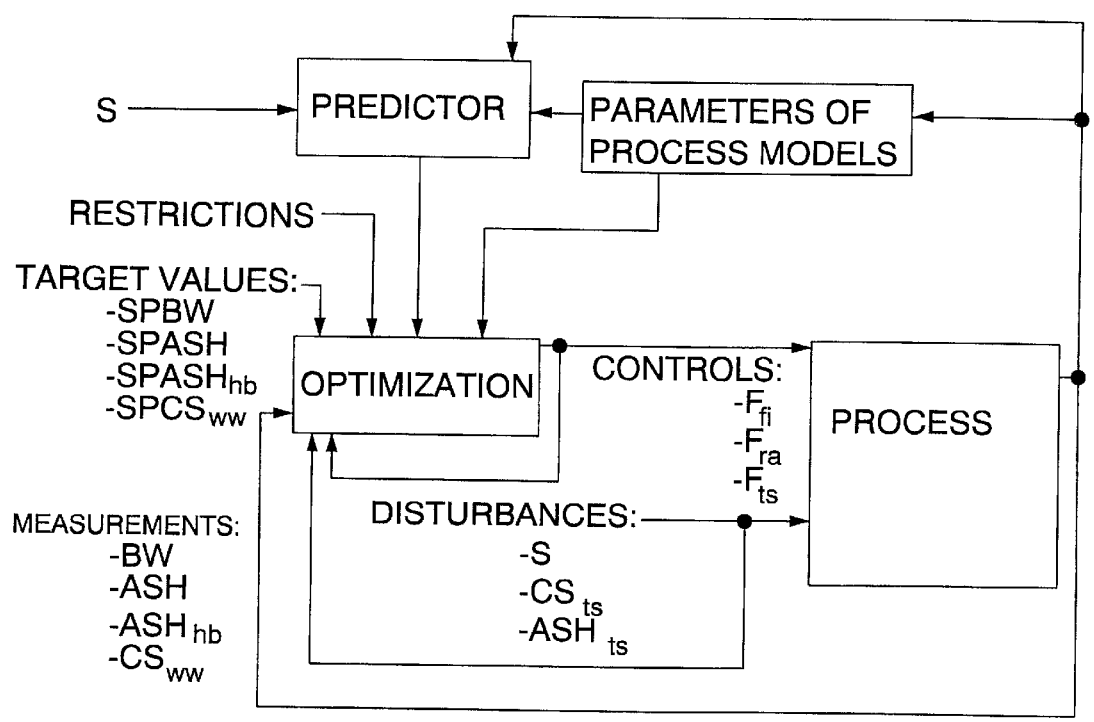
FIG. 2 shows a diagram for the structure of optimization according to the invention.

FIG. 2 shows a structure of optimizing the control arrangement according to the invention. Parameters of process models include the necessary coefficients and time constants, which have been determined by utilizing both knowledge obtained from designing a paper machine and process tests carried out at different operating points. Models used by a predictor may be different from those used for the optimization. The predictor may calculate a new model for the optimization during each round of execution, and the model takes into account changes occurring in the speed S and the production rate $PS_{ts}$ and changes that will take place in the future and that may be known in advance for example during a grade change. Determining a model is known per se to a person skilled in the art and therefore it is not discussed in greater detail in this connection. The predictor receives as input a disturbance variable that is the machine speed S, and the predictor takes it into account in case of change and provides for optimization a model which is in a required form and which takes into account the change in the speed. The disturbance variable may also be the production rate $PS_{ts}$, in which case $$PS_{ts}=F_{ts}*CS_{ts},$$

wherein $PS_{ts}$ is the production rate,
$F_{ts}$ is the stock flow, and
$C_{ts}$ is the total consistency of stock.

During optimization the controls are optimized based on the models, separate stored controls, measurements, disturbance variables and restrictions.

The optimization is a block with rather simple operation utilizing the models that are produced by the predictor and that describe for example the effect of a change in the flow of retention agent and filler on the paper ash content and on the white water total consistency. The predictor provides a prediction and produces a new process model for the optimization. The predictor contains diverse functions and takes into account different situations and changes therein from various aspects. For example, the predictor takes into account the effect of variation in the machine speed and/or the draw on the basis weight of the paper. Further, a part of the web edge is typically cut off and returned to the wire pit silo, and if changes occur in the size of the section that was cut off, the predictor takes into account and predicts the resulting change in the white water total consistency.

The target values include the basis weight SPBW, the paper ash content SPASH, the headbox ash content $SPASH_{hb}$ and the white water total consistency $SPCS_{ww}$.

A process model is a dynamic model having as input variables the stock flow $F_{ts}$ the total consistency of stock $CS_{ts}$, the flow of retention agent $F_{ra}$, the speed of the paper machine S and possibly also the stock ash content $ASH_{ts}$ and the flow of filler $F_{fi}$. Output variables of the dynamic process model include the white water total consistency $CS_{ww}$ and the basis weight of the paper BW and, if desired, the headbox ash content $ASH_{hb}$ and the paper ash content ASH. Control variables used in an optimal control include the stock flow $F_{ts}$ and the flow of retention agent $F_{ra}$. In such a case, it is possible to control simultaneously the stock flow $F_{ts}$ and the flow of retention agent $F_{ra}$, which means that the control is rapid and effective. These flows can be compensated for by utilizing either the machine speed S or the production rate $PS_{ts}$, if desired. It is also possible to use the flow of filler $F_{fi}$ simultaneously as a control variable so that the adjustment of different paper properties, including the ash content, can be controlled very well. It is possible to predict, by means of a dynamic model, the future values of the output variables, based on the existing operating point and the previous values of the input variables if there are no new changes in the control.

A model-based optimal control algorithm calculates a guide value trajectory for a control variable on the basis of the target value trajectory of the controls and the predicted output variables, and this guide value trajectory guides the process optimally to the target values in the desired manner at each moment. This data is forwarded to an automation system. An essential feature of the method used is that the optimal control algorithm is independent of the dynamic model used, and during each control round it is possible to use a dynamic model that is determined separately and the optimal control algorithm may utilize different weighting coefficients in different situations during a run and in principle during each control round. Such an arrangement is particularly important during grade changes where this type of operation makes it possible to predict the situation at each moment.

In a normal situation, each of the four target values can be assigned a set value, but in the optimization the paper ash content ASH is weighted more than the headbox ash content ASHhb. Alternatively, it is possible to take into account the paper ash content ASH but to disregard the headbox ash content $ASH_{hb}$. During a break, the headbox ash content $ASH_{hb}$ can be assigned a set value and the paper ash content ASH can be disregarded entirely. After the break, normal operation is resumed. On the other hand, during a break the paper ash content ASH can be replaced with a value provided by the model during the break, and normal operation that is based on measurements can be resumed after the break. Further, the process control can be implemented by means of the model according to the invention such that the value of the total headbox consistency is utilized during a break.

The drawings and the related description are only intended to illustrate the inventive idea. The details of the invention may vary within the scope of the claims.

What is claimed is:

1. A method for controlling properties of paper produced by a paper making machine, said method comprising providing a flow of paper stock, supplying the paper stock to a headbox, measuring flow of the paper stock, conveying the paper stock from the headbox to a former section in which a paper web is produced and from which white water is expelled, producing paper from the paper web, measuring properties of the paper including basis weight, combing the white water into the paper stock, adding a flow of filler to the paper stock, adding a flow of retention agent to the paper stock, the white water, the paper stock and the paper having respective amounts of ash content, said method comprising a control system including a dynamic model and control variables, said model relating the effect of the flow of retention agent and the paper stock flow on the basis weight of the paper to adjust, on the basis of said model, the basis weight by simultaneously controlling the flow of retention agent and the stock flow, the control system comprising predictor and optimization steps, in which the predictor step takes into account operating variables and said model and provides a prediction on the basis thereof, and the optimization step utilizes the prediction produced by the predictor step to optimize the control variables.

2. A method according to claim 1, further comprising the steps of including in said model the effect of the flow of retention agent and the flow of filler on the paper ash content and on the amount of filler in the white water and adjusting, on the basis of said model, the amount of filler in the white water and the paper ash content by simultaneously controlling the flow of retention agent and the flow of filler.

3. A method according to claim 2, wherein the model comprises as input variables the stock flow, the consistency of stock, the flow of retention agent, the flow of filler and the speed of the paper machine, and the output variables include the headbox ash content, the white water consistency, the basis weight of the paper and the paper ash content, and the control variables include the flow of filler, the flow of retention agent and the stock flow.

4. A method according to claim 3, wherein the input variables of the model also include the stock ash content.

5. A method according to claim 1, wherein the model comprises as input variables the stock flow, the consistency of stock, the flow of retention agent and the speed of the paper machine, and the output variables include the white water consistency and the basis weight of the paper, and the control variables include the flow of retention agent and the stock flow.

6. A method according to claim 5, wherein the input variables of the model also include the stock ash content.

7. A method according to claim 1, wherein the predictor step produces a new process model for optimization during each control cycle.

8. A method according to claim 1, wherein said prediction step provides a dynamic model on the basis of the prediction.

9. Equipment for controlling properties of paper produced by a paper making machine comprising a headbox into which paper stock is supplied and from which the paper stock is fed to a former section which produces a paper web from the stock, said web being dried and supplied as paper to a measuring beam at which basis weight of the paper is measured, said former section having an outlet for white water expelled during production of the paper web, means for measuring flow of the paper stock, means for combining the white water into the paper stock, means for adding a flow of filler to the paper stock, means for adding a flow of retention agent to the paper stock, the white water, the paper stock and the paper having respective amounts of ash content, said equipment comprising a control system including a model and control variables relating the effect of the flow of retention agent and the stock flow on the basis weight of the paper, and means for controlling simultaneously, based on said model, the flow of retention agent and the stock flow in order to adjust the basis weight of the paper, the control system further including a predictor means which, comprises means for taking into account said model and operating variables for producing a prediction output and an optimization means for utilizing said prediction output for optimizing the control variables and the process of producing the paper.

10. Equipment according to claim 9, wherein the a model includes the effect of the flow of retention agent and the flow of filler on the white water consistency and on the paper ash content, and the control means further comprises means for simultaneously controlling, on the basis of said model, the flow of retention agent and the flow of filler in order to adjust the white water total consistency and the paper ash content.

11. Equipment according to claim 10, wherein the model comprises as input variables the stock flow, the consistency of stock, the flow of retention agent, the flow of filler and the speed of the paper machine, and the output variables include the headbox ash content, the white water consistency, the basis weight of the paper and the paper ash content, and the control variables include the flow of filler, the flow of retention agent and the stock flow.

12. Equipment according to claim 11, wherein the input variables of the model also include the stock ash content.

13. Equipment according to claim 9, wherein the model comprises as input variables the stock flow, the consistency of stock, the flow of retention agent, the flow of filler and the speed of the paper machine, and the output variables include the headbox ash content, the white water consistency, the basis weight of the paper and the paper ash content, and the control variables include the flow of retention agent and the stock flow.

14. Equipment according to claim 13, wherein the input variables of the model also include the stock ash content.

15. Equipment according to claim 9, wherein said predictor means includes means for producing a further model on the basis of the prediction output.

* * * * *